(12) United States Patent
Herman et al.

(10) Patent No.: US 6,889,872 B2
(45) Date of Patent: May 10, 2005

(54) ELECTRIC TWO-PART MATERIAL DISPENSER

(75) Inventors: Timm Herman, Ellicottville, NY (US); Kevin Whited, Ellicottville, NY (US); Raymond Fritz, Northfield, OH (US)

(73) Assignee: Meritool, L.L.C., Ellitcottville, NY (US)

( * ) Notice: Subject to any disclaimer, the term of this patent is extended or adjusted under 35 U.S.C. 154(b) by 0 days.

(21) Appl. No.: 10/610,081

(22) Filed: Jun. 30, 2003

(65) Prior Publication Data

US 2004/0045982 A1 Mar. 11, 2004

Related U.S. Application Data

(60) Provisional application No. 60/392,418, filed on Jun. 28, 2002, and provisional application No. 60/409,444, filed on Sep. 10, 2002.

(51) Int. Cl.⁷ .................................................. B67D 5/00
(52) U.S. Cl. ...................... 222/82; 222/137; 222/145.5; 222/333
(58) Field of Search ....................... 222/82, 137, 145.5, 222/145.6, 333

(56) References Cited

U.S. PATENT DOCUMENTS

| | | |
|---|---|---|
| 1,829,789 A | 11/1931 | Dammeyer |
| 3,854,629 A | 12/1974 | Blieberger |
| 3,861,567 A | 1/1975 | Davis, Jr. |
| 4,024,994 A | 5/1977 | Davis, Jr. |
| 4,171,072 A | 10/1979 | Davis, Jr. |
| 4,180,187 A | 12/1979 | Ben-Haim |
| 4,249,677 A | 2/1981 | Davis, Jr. |
| D258,797 S | 4/1981 | Davis, Jr. |
| 4,260,076 A | 4/1981 | Bergman |
| 4,264,021 A | 4/1981 | Davis, Jr. |
| 4,273,269 A | 6/1981 | Davis, Jr. |
| 4,322,022 A | 3/1982 | Bergman |
| 4,335,834 A | 6/1982 | Zepkin |
| 4,583,934 A | 4/1986 | Hata et al. |
| 4,615,469 A | 10/1986 | Kishi et al. |
| 4,669,636 A | 6/1987 | Miyata |
| 5,027,984 A | 7/1991 | Gakhar et al. |
| 5,058,781 A | 10/1991 | Aronie et al. |
| 5,188,259 A | 2/1993 | Petit |
| 5,323,931 A | 6/1994 | Robards, Jr. et al. |
| 5,341,958 A | 8/1994 | Bayat et al. |
| 5,503,307 A | 4/1996 | Wilson et al. |
| 5,556,009 A | 9/1996 | Motzko |
| 5,775,539 A | 7/1998 | Bates et al. |
| 5,897,028 A * | 4/1999 | Sauer .......................... 222/82 |
| 6,012,610 A * | 1/2000 | Pauser et al. ................. 222/88 |
| 6,056,165 A * | 5/2000 | Speranza ..................... 222/333 |
| 6,089,407 A | 7/2000 | Gardos |
| 6,311,871 B1 * | 11/2001 | Binder ..................... 222/145.6 |
| 6,488,180 B1 * | 12/2002 | Bayat ......................... 222/137 |
| 6,524,102 B2 * | 2/2003 | Davis ........................... 433/32 |

FOREIGN PATENT DOCUMENTS

| | | |
|---|---|---|
| CA | 1118729 | 2/1982 |
| DE | 3418052 | 12/1984 |
| DE | 3428202 | 2/1985 |
| DE | 3811954 | 10/1989 |
| EP | 0343003 | 11/1989 |

* cited by examiner

*Primary Examiner*—Joseph A. Kaufman
(74) *Attorney, Agent, or Firm*—Watts Hoffman Co., L.P.A.

(57) ABSTRACT

An electric dispensing gun for dispensing two part viscous materials. The dispensing gun features a directly driven pinion/rack assembly and an optional mixing manifold for dispensing material from sausage packaging. A controller controls operation of the dispensing gun to implement dosage control and automatic power reverse features.

40 Claims, 4 Drawing Sheets

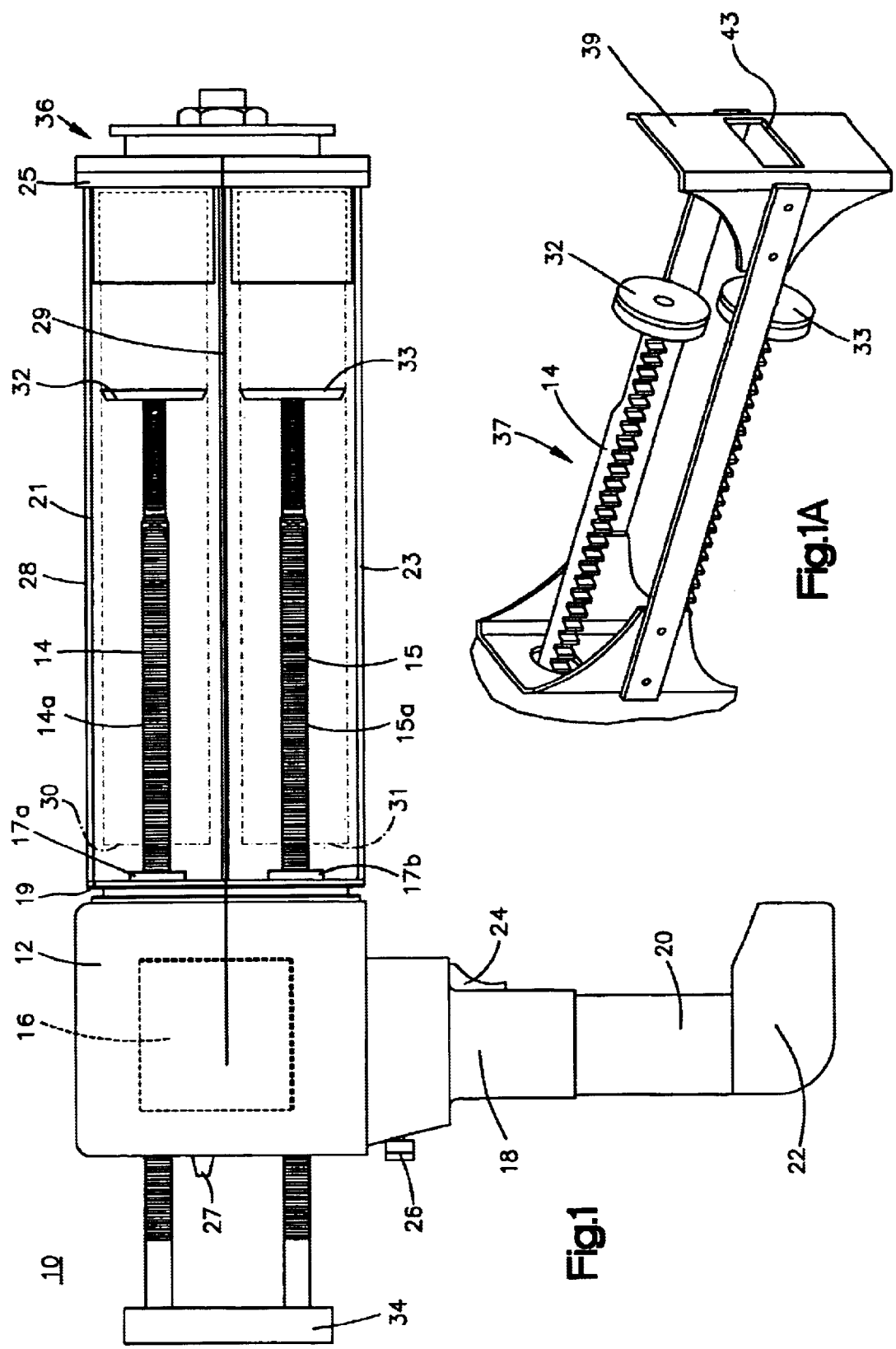

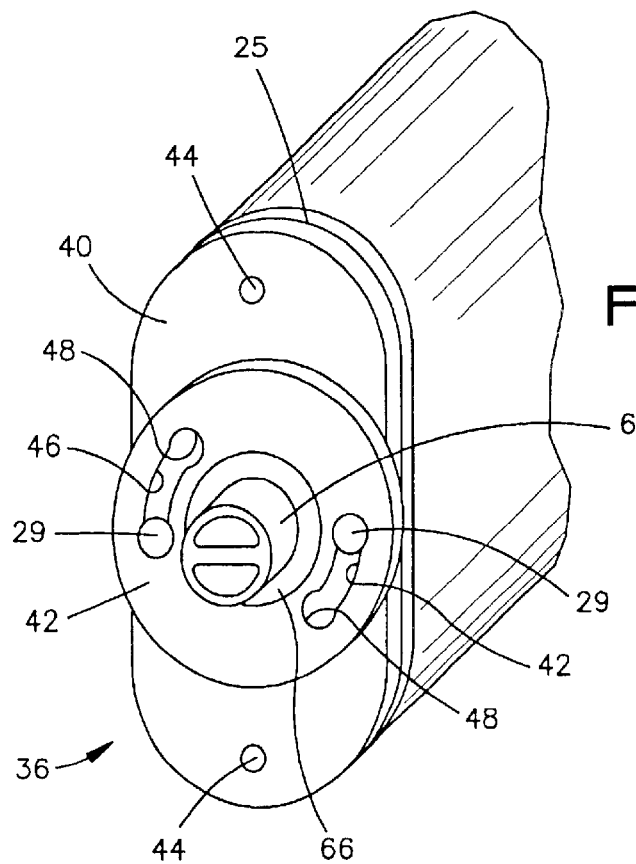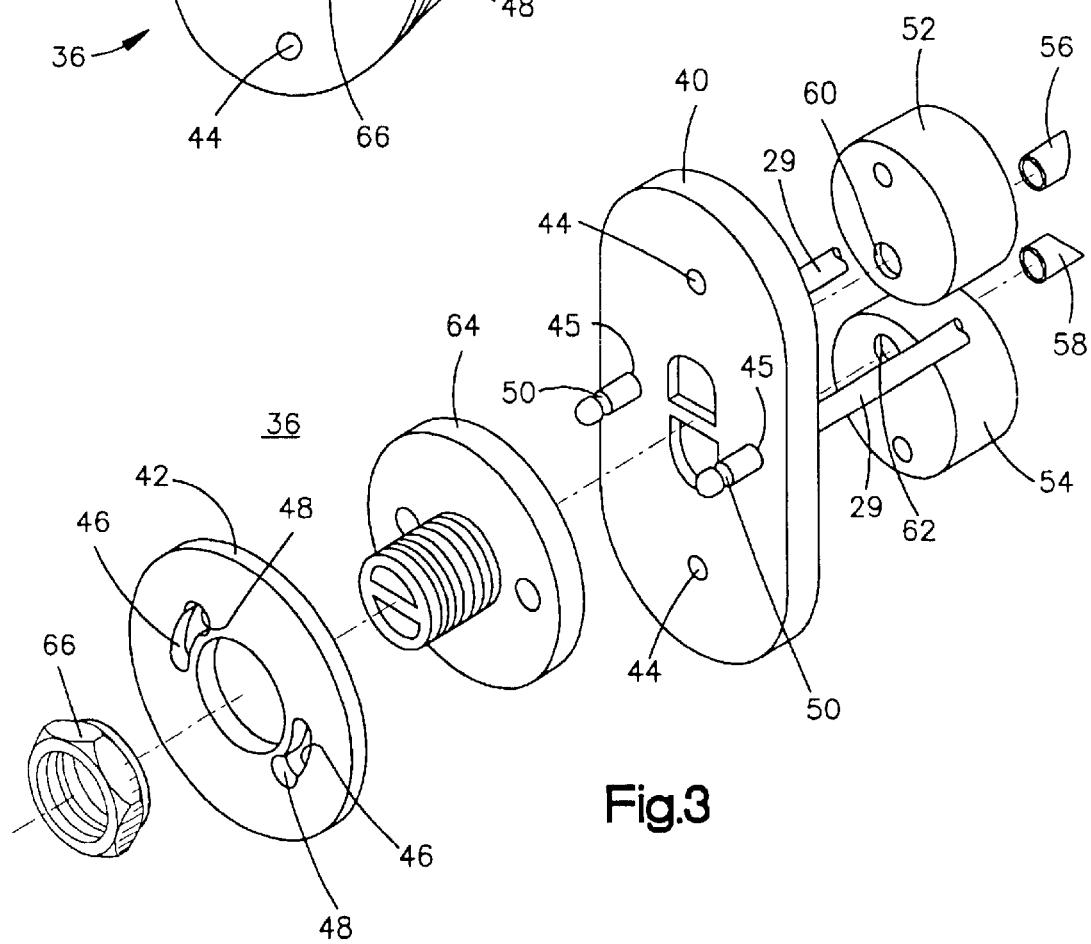

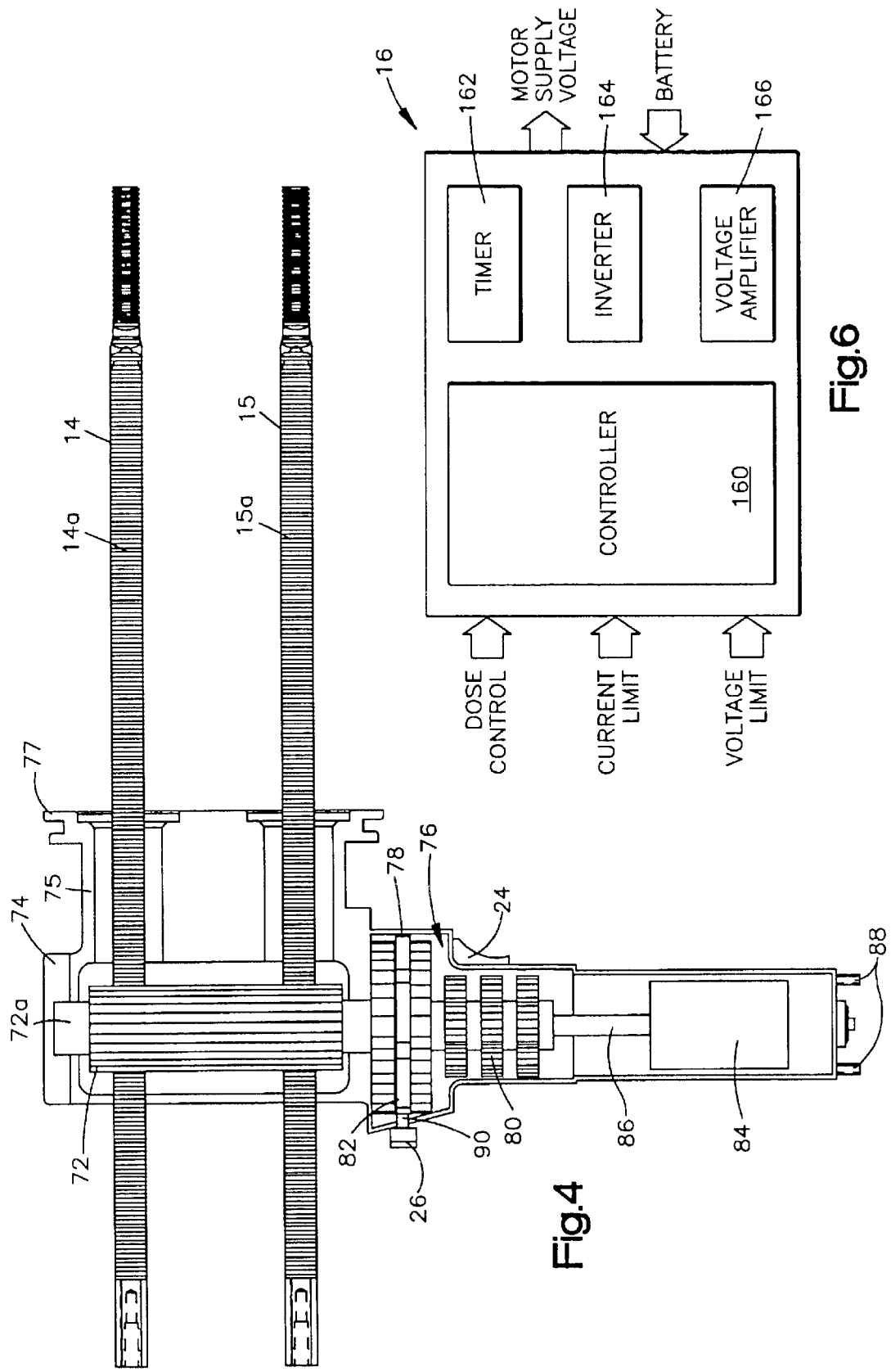

ELECTRIC TWO-PART MATERIAL DISPENSER

This application claims benefit of provisional application No. 60/392,418 Jun. 28, 2002 and claims of No. 60/409,444 Sep. 10, 2002.

TECHNICAL FIELD

This invention relates to viscous material dispensers and in particular to a material dispensing gun adapted to receive a disposable tubes of constituent viscous materials either in cartridge or sausage packaging that are mixed upon dispensing into a resulting adhesive or sealant material.

BACKGROUND OF THE INVENTION

Power viscous material dispensers such as caulking guns that are driven by various power sources such as compressed air or electric motors are well known in the art. One commercially successful power caulking gun is disclosed in U.S. Pat. No. 5,775,539 to Bates et al., which is incorporated herein by reference in its entirety. The caulking gun described in the '539 patent includes an electric motor that drives a piston carrying rack through a combination of planetary, bevel, and pinion gears. The electric motor is retained in a housing that protrudes from the rear of the gun and the motor shaft rotates about an axis that is parallel to the length of the piston carrying rack.

Many adhesive materials are sold as two constituent materials, or parts, that are mixed together upon application to form a single adhesive material. Electric dispensing guns have been developed to dispense two part adhesives. For example, U.S. Pat. No. 6,089,407 to Gardos describes a fluid material dispensing gun for dispensing two part materials for dental use that has in-line longitudinal racks for driving a piston into each of the constituent fluids, which are then concurrently dispensed through a single orifice. This dispensing gun has racks that are driven by an electric motor through a series of bevel gears and a pinion gear that rotates about an axis perpendicular to the axis of rotation of the motor.

SUMMARY OF THE INVENTION

A dispenser for dispensing two part viscous material. The dispenser can accept constituent materials in flexible sausage packaging or rigid cartridge form. An electric motor drives a pinion gear that is coaxial with the motor shaft. The pinion gear in turn drives two parallel spaced racks that each have a piston at a distal end for applying force to the constituent materials. The constituent materials are dispensed by the pistons through a dispensing orifice. In an embodiment that dispenses constituent materials from sausage packaging a manifold is included that directs material from each sausage to single nozzle on the dispenser.

In an exemplary embodiment, the motor is mounted in the handle of the dispenser and planetary gears are interposed between the motor and the pinion to provide gear reduction in an in-line package. A control circuit controls operation of the dispenser based on preset parameters and inputs. The controller performs a dose control function by using a timer to discontinue motor operation after a preset amount of time has passed. The preset time for the dose control function can be set by the user or by the controller based on an estimated amount of material that has been dispensed as calculated by the controller. The controller uses motor voltage and current to estimate the amount of material that has been dispensed by mapping motor voltage to rack speed and motor current to material viscosity.

The controller limits voltage and current to the motor to maintain dispenser functioning within preset parameters. The controller reverses the motor at the end of each application to relieve pressure on the pistons and the resulting fluid overflow. In a reload cycle, the controller may place a voltage amplifier in series with the motor to cause the motor to move the rack in a reverse direction at a relatively high speed to facilitate reloading.

BRIEF DESCRIPTION OF THE DRAWINGS

FIG. 1 is a side perspective view of the novel and improved dispenser of the present invention;

FIG. 1A is side view of an optional cartridge holder.

FIG. 2 is an enlarged and perspective view of the outlet of the present dispenser;

FIG. 3 is and exploded view of the components of the dispenser at its outlet end;

FIG. 4 is a view of the dispenser of FIG. 1 with the gearing enclosure removed;

DETAILED DESCRIPTION

Figure 5:
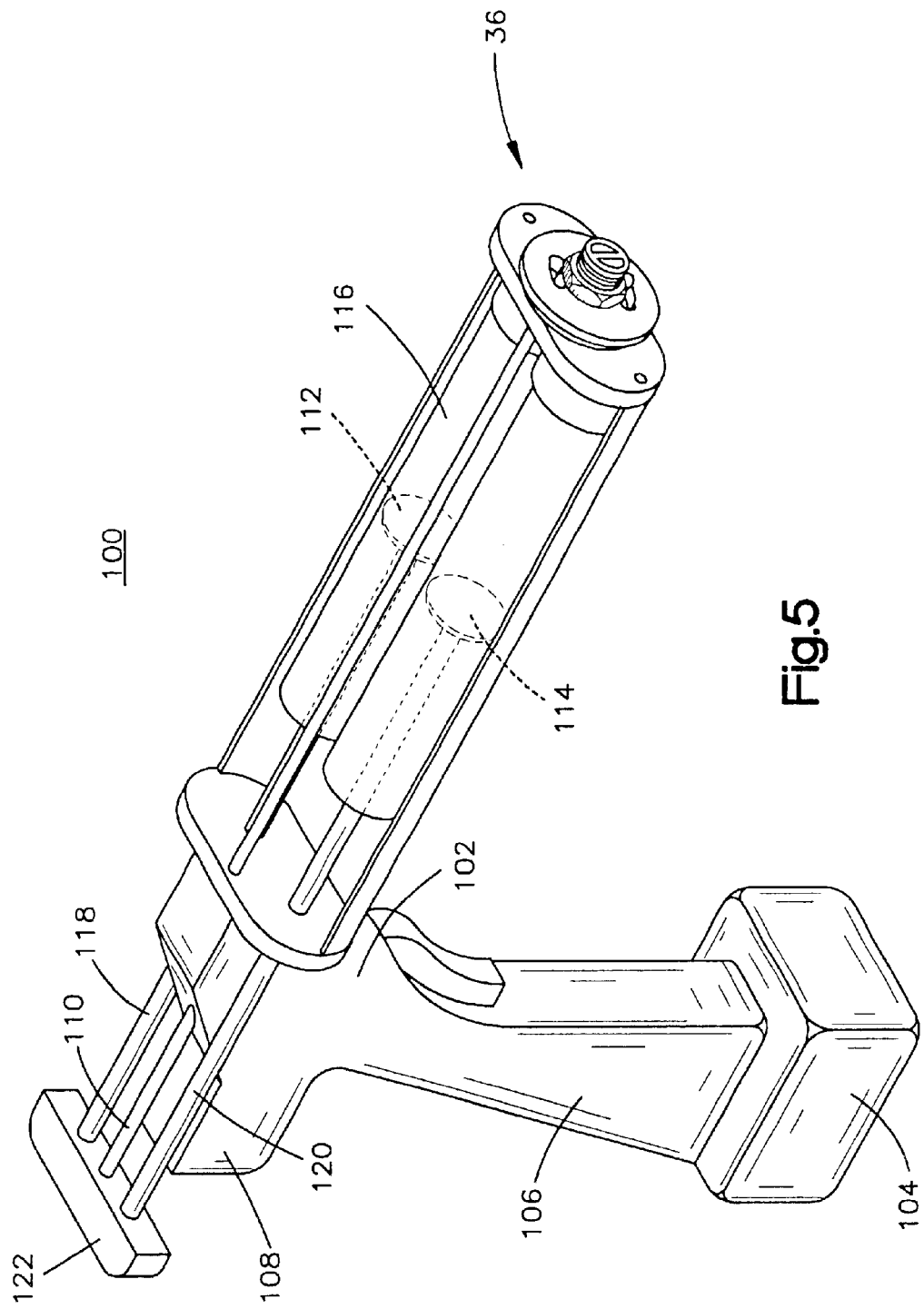
FIG. 5 is a perspective view of an alternative embodiment incorporating the dispensing end of the present invention; and, FIG. 6 is block diagram a of control circuit for use in an embodiment of the present dispenser.

Turning now to the figures, FIG. 1 illustrates a new and improved dispensing gun 10 of the present invention. The gun 10 includes a pinion gear enclosure 12 that houses a pinion gear (shown in FIG. 4) which propels drive racks 14, 15. The enclosure 12 additionally houses circuitry that controls the movement of the drive racks. The circuitry is mounted within the enclosure 12 at the location indicated by reference character 16. The pinion gear is driven by a plurality of planetary gears (shown in FIG. 4) housed in a planetary gear enclosure 18. The planetary gears are driven by an electrical motor located in the motor housing 20 which is supplied electrical current by battery 22. The planetary gear housing 18 and motor housing 20 additionally are housed within a handle that is gripped by an operator during operation of the dispensing gun 10. A portion of gear housing 18 supports a trigger 24 which activates the motor to supply power to the planetary gears and pinion gear to propel the racks 14, 15. In addition, a clutch lever 26 extends through a portion of the gearing enclosure 18. The pinion enclosure 12 also supports a dosing-speed control knob 27 that is in communication with the circuitry for controlling the movement of the racks 14, 15. The racks 14, 15 include a plurality of teeth shown generally by reference characters 14a, 15a which engage the pinion gear to drive the racks 14, 15.

A cartridge holder 28 is fastened to the pinion enclosure 12 such that cartridges (shown in phantom) 30, 31 are aligned with the racks 14, 15. The cartridge holder 28 includes a rear plate 19 that secures the cartridge holder to the gear housing 12 via two cartridge nuts 17a, 17b. The rack 14 extends through the bore of nut 17a and the rack 15 extends through the bore of nut 17b. Side plates 21, 23 extend from the rear plate 19 generally parallel to each other for the length of the cartridges 30, 31 and are coupled to a front plate 25. Bottom rods 27 extend from the rear plate 19 through a front plate 25. A dispensing unit 36 may be affixed to the front plate 25 and is further discussed below with respect to FIGS. 3 and 4.

The cartridges 30, 31 may either resemble sausages in that each has one of parts A or B within a flexible plastic skin or rigid tubes containing the material. When the sausage type cartridges are employed, the dispensing unit 36 is attached to better accommodate the sausage type packaging of the material. However, where rigid tubes are employed, the dispensing unit 36 is removed and the standard end of the commercial two-part packaging is used in place of the dispensing unit 36. During rigid commercial tube usage, an optional cartridge holder 37 may be employed (see FIG. 1a). The optional cartridge holder 37 includes a front plate 39 which has a bore 43 that provides clearance for the dispensing end of the two-part commercial tubes. Pistons 32, 33 are affixed to the drive end of the racks 14, 15 for compressing material from the cartridges 30, 31 as the racks 14, 15 are driven by the pinion gear. Additionally, the racks 14, 15 are coupled together by a return handle 34 located at an opposite end of the racks 14, 15 from the drive direction. The return handle 34 is used to pull the racks 14, 15 and coupled pistons 32, 33 out of the cartridge tubes 30, 31 when the tube is empty or when different tubes are desired. The return handle 34 can also act as a hanger hook for hanging the gun 10 during storage.

Tuning now to FIGS. 2 and 3, the distal end of the cartridge holder is shown illustrating the dispensing unit 36. The dispensing unit 36 includes a manifold 40 which is removably attachable to the front plate 25 of the cartridge holder 28 by locking ring 42. Rods 29 extend through the manifold 40, nozzle adapter 64 and locking ring 42 for securing the dispensing unit 36 to the cartridge holder 28. The locking ring 42 selectively engages the rods 29 in arcuately curved locking slots 46 provided in the locking ring 42. More specifically, the locking slots 46 have enlarged ends for receipt of forward ends of rods 29. Once the enlarged ends 48 of the locking ring 42 have been telescoped over of the rods 29, rotation of the ring in a clockwise direction brings arcuate sections of the slots 46 into circumferential grooves 50 located at the dispensing end of the rods 29.

As best seen in FIG. 3, and understood by reference to FIG. 1, the manifold 40 carries a pair of piston cups 52, 54 attached via a bolt through securing holes 44. The piston cups co act with the pistons at their end of travel to provide a sealed space for the material that remains in the sausage to reduce leakage of material back into the cartridge holder. The piston cups 52, 54 respectively receive and carry removable piercing tubes 56, 58. The piercing tubes 56, 58 are respectively aligned with outlet ports 60, 62 in the piston cups 52, 54.

In operation, cartridges of the A and B materials are inserted into the cartridge holder 28, and the piston cups 52, 54 with their piercing tubes 56, 58. The loading of the cartridges is accomplished at a time when the pistons 32 and drive racks 14 are all retracted. Once the locking ring 42 and manifold 40 are back in place, the rack 14 is advanced to press forward the pistons 32 into the forward ends of the cartridges which further press into the piston cups 52, 54. As the cartridges enter the piston cups 52, 54 the piercing tubes 56, 58 pierce the respective cartridges. Motor driven advance of the rack 14 causes the material from the two cartridges to be dispensed through the manifold 40 and the nozzle adaptor 64 and, as they are dispensed to be concurrently mixed for their intended purposes. In an alternative embodiment, the nozzle adaptor 64, the manifold 40, the piston cups 52, 56, and the piercing tubes 56, 58 are a single molded unit that can be removed and discarded when a new type of material is to be dispensed.

Referring now to FIG. 4, a view of the pinion gear and planetary gear is shown with their respective enclosures removed. The pinion gear 72 is supported in a pinion gear housing 74. The pinion gear 72 may be secured in the housing 74 by any means as know to those of ordinary skill in the art. The gear housing includes an extension 75 which further includes a mounting plate 77 for mounting the cartridge holder 28 (shown in FIG. 1). The gear housing 74 further includes guide depressions (not shown) which guide tracks 14 and 15 through the gear housing 74. Tracks 14 and 15 extend through the pinion gear housing 74 in a manner such that the teeth 14a, 15a engage teeth 72a of the pinion gear 72. The pinion gear 72 is coupled to a system of planetary reduction gears (generally referred to as reference character 76). The system 76 includes a first larger set 78 and a second small set 80 of planetary gears. The larger set 78 includes two stages of planetary gears coupled together by ring gear 82. The smaller set 80 includes three stages of planetary gears. The planetary gear system 76 is coupled to the motor 84 through a drive shaft 86. Further, a battery (shown in FIG. 1) supplies current to the motor 84 through conductors 88.

During operation, the motor turns the drive shaft at about 1500 rpm thus rotating the planetary gear system 76. Each stage of the gear system reduces the drive speed at approximately a 3:1 ratio. The planetary gears of the gear system 76 operate in a manner consistent with the planetary gear system disclosed in U.S. Pat. No. 5,775,539 to Bates et al. The planetary gears are coupled between the pinion gear 72 and the drive motor such that the drive speed being imparted on the pinion gear 72 is reduced to a point suitable for driving racks 14, 15 for dispensing material from cartridges (shown in FIG. 1). The motor 84, motor shaft 86, planetary gears 76 and pinion gear 72 are located on the same axis coincident to each other which allows for a more efficient and durable dispensing system.

Once the cartridges are emptied or new cartridges are desired, racks 14, 15 must be returned to the starting position in order to remove the cartridges. One way to return racks 14, 15 is through use of clutch lever 26. Clutch lever 26 supports a plunger 90 which engages the ring gear 82. When the lever 26 is in the locked position, the unit drives forward for normal dispensing operation. When the clutch lever 26 is in the unlocked position, the racks 14, 15 can be manually retracted to any position desired by the operator. The clutch and clutch lever operate in a manner consistent with FIGS. 5 and 6 of U.S. Pat. No. 5,775,539 to Bates et al.

Referring now to FIG. 5, an alternative dispenser is shown incorporating the dispensing unit 36 of the present invention. The dispenser 100 includes a molded body 102. A battery 104 is coupled to a handle portion 106 of the body 102. The battery 104 provides energy to drive a motor within a motor portion 108 of the body 102. A drive train, not shown, connects the output of the motor to a drive rod 110. The drive rod 110 in turn drives a spaced and generally parallel pair of piston rods 118, 120. The piston rods 118, 120 respectively drive a spaced pair of pistons 112, 114. The piston rods 118, 120 and the drive rod are all connected to a return handle 122.

The pistons 112, 114 are respectively reciprocal within a housing 116 which is contoured to retain a pair of material cartridges, not shown. A dispensing unit 36 as previously disclosed in FIGS. 2 and 3 is coupled to the dispensing end of the body 116.

Control Circuit

Referring to FIG. 6, a simplified block diagram of the control circuit 16 is shown. The control circuit controls the flow of battery voltage to the motor based on preset parameters and control algorithm logic that is stored in a controller 160. There are four adjustable inputs to the control circuit 16: dose control, current limit, trigger level, and voltage limit. In the described embodiment, the dose control input is set by the user via knob 27 (FIG. 1) and the current and voltage limits are internal potentiometers that are set during manufacture of the dispenser unit. However, the current and voltage limits could be made accessible to the user by placing knobs or other means on the exterior of the dispenser. The voltage limit controls the maximum speed of the motor, and correspondingly, the flow rate of the material out of the dispenser. The current limit controls the amount of force that can be applied by the pistons to prevent damage to dispenser caused by excessive forces acting within the dispenser. The control circuit 16 controls the motor supply voltage such that the motor voltage and motor current are maintained below the preset limits.

The trigger level input is variable input that corresponds to an amount of displacement of the trigger that is actuated by the user to control the flow of material from the dispenser. The higher the trigger displacement, the higher the voltage that is supplied to the motor. A dose control feature is implemented using a timer circuit 162 that is activated by a signal on the trigger level input. The timer circuit signals the controller to discontinue power to the motor after an amount of time that is set by the dose control knob has passed. This feature allows a user to apply a uniform amount of material with each trigger actuation by setting the desired amount of application time and actuating the trigger until the motor stops for each application. In an alternative embodiment, if the dose control feature is actuated, the controller will supply voltage to the motor for the preset dosage time each time the trigger is actuated regardless of the length of time the trigger is actuated. The dose control feature can be disabled by turning the dose control knob 27 to an OFF position. When the dose control feature is disabled, the motor supply voltage is controlled solely by the displacement of the trigger.

When the motor supply voltage is discontinued, it is desirable to relieve the pressure on the material within the dispenser to prevent continued flow out of the dispenser after the desired amount of material has been dispensed. To achieve this end, the controller 160 is in communication with an inverter circuit 164 that inverts the voltage to the motor for a preset time to cause it to reverse direction and move the racks and pistons away from the dispensing end of the dispenser. Another way to prevent unwanted flow at the end of an application cycle is to discontinue power to the motor prior to the end of the dose time limit set by the dose control knob 27 so that the continued flow becomes part of the application cycle.

Prior to reloading the dispenser unit with new material cartridges or sausages, it is necessary to return the racks to the load position. As already discussed, this can be accomplished by actuating the clutch and manually pulling the racks back to the load position. The controller 160 can cause the racks to return quickly to the load position by inverting the voltage to the motor to reverse rack travel direction and placing a voltage amplifier 166 in series with the motor that boosts the supplied voltage several times to increase the speed of the racks. This reload positioning cycle can be actuated by the user via a button on the exterior of the dispenser. In another embodiment, the end of rack travel in the dispense direction can be sensed by monitoring motor current or rack position and when the end of rack travel is reached activating the rack reload positioning. In addition to reversing rack travel at increased speed to release spent cartridges, the voltage amplifier may also be activated to quicly propel the racks into engagement with a new cartridge. The voltage amplifier would be deactivated upon engagement with the cartridge, sensed by an increase in current draw or rack position.

A more sophisticated dose control feature that provides an application cycle that results in a uniform amount of material being dispensed with each trigger actuation can be accomplished by programming the controller to estimate an amount of fluid that has been dispensed in any given trigger actuation by monitoring motor current, motor voltage, and time. Within the controller, the motor voltage is correlated to a rack speed and the motor current is correlated to a piston force and in turn material viscosity. The rack speed can be multiplied by the time duration to approximate an amount of material that has been dispensed. The amount of dispensed material can be compared against the desired amount that is set by the dosage control knob and this information may be used to update the time duration of the application cycle. The duration of time of the application cycle can also be continuously updated by the controller based on the estimated material viscosity (determined based on motor current) such that more viscous materials have a longer duration of time in the application cycle.

Although the present invention has been described with a degree of particularity, it is the intent that the invention include all modifications and alterations from the disclosed design falling within the spirit or scope of the appended claims.

We claim:

1. A hand held viscous fluid dispenser for dispensing a two-component viscous material comprising:
    an electric drive motor including a motor shaft having a shaft axis of rotation;
    a pinion gear driven by the motor having a pinion axis of rotation that is generally parallel to and coincident with the shaft axis of rotation;
    a pair of parallel, spaced racks that directly engage and are driven by the pinion gear;
    a piston connected to a distal end of each of the racks for applying force to a component viscous material container to dispense viscous fluid contained therein; and
    a chamber that encases the pistons and racks for retaining the component viscous material containers in engagement with the pistons and wherein the chamber has an orifice at a dispensing end through which the two-component viscous material flows.

2. The dispenser of claim 1 further including a handle disposed generally perpendicular to the chamber and adapted to be gripped by an operator.

3. The dispenser of claim 2 wherein the electric drive motor is housed within the handle.

4. The dispenser of claim 2 wherein the electric drive motor is housed in a motor housing such that the axis of rotation of the motor shaft is perpendicular to the handle.

5. The dispenser of claim 3 wherein a planetary drive is carried by the handle and interposed between the shaft and the pinion.

6. The dispenser of claim 5 wherein the shaft, the driver and the pinion are axially aligned.

7. The dispenser of claim 1 further including a controller in electrical communication with the electric motor for controlling operation of the dispenser.

8. The dispenser of claim 7 further including the controller comprises a voltage control module that limits a level of voltage that is supplied to the electric motor.

9. The dispenser of claim 7 further including the controller comprises a current control module that limits a level of current that can be drawn by the electric motor.

10. The dispenser of claim 7 wherein the controller includes a dose control module that, once activated, powers the electric motor to dispense a predetermined amount of viscous fluid.

11. The dispenser of claim 10 wherein the dose control module includes a timer circuit that, once activated, disconnects power from the electric motor after a preset time.

12. The dispenser of claim 10 wherein the dose control module estimates an amount of material dispensed by:
   monitoring a voltage level being supplied to the motor;
   mapping the voltage level to a motor speed;
   determining an amount of fluid being dispensed per unit time based on the motor speed; and
   multiplying the amount of material being dispensed per unit time by an elapsed time to estimate the amount of fluid that has been dispensed.

13. The dispenser of claim 12 wherein the controller discontinues motor operation when the estimated amount of material equals a preset dose amount.

14. The dispenser of claim 12 wherein the dose control module monitors a current level being supplied to the motor and maps the current level to an estimated material viscosity.

15. The dispenser of claim 14 wherein the dose control module adjusts a dosage time based on the estimated material viscosity.

16. The dispenser of claim 15 wherein the controller discontinues motor operation when the elapsed time equals the dosage time.

17. The dispenser of claim 8 wherein the voltage control module controls voltage based on input from a potentiometer.

18. The dispenser of claim 9 wherein the current control module controls current based on input from a potentiometer.

19. The dispenser of clam 1 including a set of planetary gear stages interposed between the motor shaft and pinion gear that reduce the speed of the motor shaft.

20. The dispenser of claim 19 including a clutch that selectively engages a planetary gear set to drive the racks toward the orifice.

21. The dispenser of claim 1 wherein the chamber includes a manifold for directing fluid from each component fluid container to the dispensing orifice.

22. The dispenser of claim 21 wherein the manifold includes piercing elements for piercing flexible sausage pack component viscous fluid containers.

23. The dispenser of claim 1 wherein the manifold includes a piston cup that receives the piston when the rack is in a fully extend position to create a seal around any remaning fluid in the component vicscous material container.

24. The dispenser of claim 1 wherein the motor is powered in response to actuation of a trigger by an operator.

25. The dispenser of claim 1 wherein the shaft and pinion axes are axially aligned.

26. The dispenser of claim 7 wherein the controller causes a voltage supplied to the motor to be reversed for a preset amount of time upon deactivation of the dispenser.

27. The dispenser of claim 7 including a power reload module within the controller that, upon activation, reverses motor voltage polarity and places a voltage amplifier in communication with the motor to cause the rack to move away from the dispensing end at a relatively high rate of travel.

28. The dispenser of claim 27 wherein the power reload module is activated by an external switch on the dispenser.

29. The dispenser of claim 27 wherein the power reload module is activated by a sensor that senses that the rack has been driven an end of travel.

30. The dispenser of claim 27 wherein the power reload module places the voltage amplifier in communication with the motor to cause the rack to move toward the dispensing end until the piston engages the component viscous material container.

31. A dispenser for two part materials comprising:
   a) structure defining a space for support of a pair of tubes each containing prior to use, a supply of a respective one of the two parts;
   b) a pair of racks each for coaction with an associated one of a pair of pistons, the pistons lack being carried by a selected one of:
      i) a respective distal end of: an associated rack and,
      ii) a tube of an associated one of the material parts;
   c) an elongated pinion engaging both racks for concurrently advancing the racks to expel material from a pair of such tubes of material supported by the structure;
   d) a handle connected to the structure and projecting laterally from the structure in a pistol grip arrangement;
   e) a battery operated electric motor carried by the handle;
   f) a battery physically connected to the handle and electrically connected to the motor selectively to energize the motor;
   g) a planetary driver operationally interposed between and connected to the motor and the pinion for transmitting rotational forces from the motor to the pinion; and,
   h) a clutch for selectively establishing a driving connection between the motor and the pinion.

32. The dispenser of claim 31 wherein the motor has an output shaft axially aligned with the planetary drive and the pinion.

33. The dispenser of claim 31 wherein the racks are manually retractable when dispensing of the two part material from a pair of tubes has been completed and such tubes are to be removed from the structure.

34. A control apparatus for controlling a drive motor in a viscous material dispenser wherein the drive motor moves a piston that engages a viscous material container in response to a trigger actuation to dispense the viscous material through a dispensing nozzle, the control apparatus comprising:
   a voltage control module for setting a threshold voltage and maintaining motor voltage at the set voltage;
   a current control module for setting a threshold current and maintaining motor current at the set voltage;
   a dose control module for controlling a dose amount that is applied during an application cycle; and
   a reload control module for controlling piston movement to facilitate unloading of a spent viscous material container and loading a new viscous material container.

35. The control apparatus of claim 34 wherein the voltage control module comprises a potentiometer that a user manipulates to set the threshold voltage.

36. The control apparatus of claim 34 wherein the current control module comprises a potentiometer that a user manipulates to set the threshold current.

37. The control apparatus of claim 34 wherein the dose control module includes a timer for discontinuing power to the drive motor after a preset amount of time has passed since trigger actuation.

38. The control apparatus of claim 34 wherein the dose control module estimates an amount of material dispensed by:

monitoring a voltage level being supplied to the motor;

mapping the voltage level to a motor speed;

monitoring a current level being supplied to the motor;

mapping the current level to an estimated material viscosity;

determining an amount of fluid being dispensed per unit time based on motor speed and material viscosity; and multiplying the amount of material being dispensed per unit time by the time elapsed since trigger actuation to estimate the amount of fluid that has been dispensed.

39. The control apparatus of claim 34 wherein the reload control module comprises a voltage amplifier that is placed in communication with the motor to provide increased motor voltage to move the pistons away from the dispensing end.

40. The control apparatus of claim 39 wherein the reload control module places the voltage amplifier in communication with the motor to provide increased motor voltage to move the pistons into engagement with the new viscous material container.

* * * * *